United States Patent [19]

Gross et al.

[11] Patent Number: 5,037,632
[45] Date of Patent: Aug. 6, 1991

[54] COMPOSITION FOR THE STRENGTHENING OF THE HAIRDO AND THE CARE OF HAIR

[75] Inventors: Paul Gross; Hildegard Henze, both of Darmstadt; Günther Lang, Reinheim; Harald Wendel, Ober-Ramstadt; Liane Stähle, Ober-Ramstadt/Wembach, all of Fed. Rep. of Germany

[73] Assignee: Wella Aktiengesellschaft, Darmstadt, Fed. Rep. of Germany

[21] Appl. No.: 415,286

[22] PCT Filed: Feb. 13, 1989

[86] PCT No.: PCT/EP89/00128
§ 371 Date: Aug. 23, 1989
§ 102(e) Date: Aug. 23, 1989

[87] PCT Pub. No.: WO89/08443
PCT Pub. Date: Sep. 21, 1989

[30] Foreign Application Priority Data

Mar. 10, 1988 [DE] Fed. Rep. of Germany ....... 3807915

[51] Int. Cl.⁵ ............................................... A61K 7/00
[52] U.S. Cl. ......................................... 424/47; 424/45; 424/61; 424/70; 424/71; 8/426
[58] Field of Search ..................... 424/71, 45, 70, 61, 424/47; 8/426

[56] References Cited

U.S. PATENT DOCUMENTS

| | | | |
|---|---|---|---|
| 3,730,182 | 5/1973 | Boghosian | 424/45 |
| 4,182,612 | 1/1980 | Sokol | 8/426 |
| 4,198,313 | 4/1980 | Bargigia | 424/45 |
| 4,551,512 | 11/1985 | Straub | 424/70 |
| 4,719,099 | 1/1988 | Grollier | 424/61 |
| 4,781,723 | 11/1988 | Gross | 424/47 |
| 4,830,850 | 5/1989 | Login | 424/45 |
| 4,834,768 | 5/1989 | Grollier | 8/426 |
| 4,865,838 | 9/1989 | Gross | 424/47 |

Primary Examiner—Thurman Page
Assistant Examiner—William E. Benston, Jr.
Attorney, Agent, or Firm—Michael J. Striker

[57] ABSTRACT

An agent for setting and caring for the hair, is based on a synergistic combination of (a) 0.1 to 10 percent by weight of a cationic copolymer of vinylimidazolium methochloride and vinylpyrrolidone as a quaternized copolymer of the vinylpyrrolidone and (b) 0.1 to 5.0 percent by weight of tetraoxyethylene laurylether.

11 Claims, No Drawings

COMPOSITION FOR THE STRENGTHENING OF THE HAIRDO AND THE CARE OF HAIR

BACKGROUND OF THE INVENTION

The present invention relates to an agent to set and care for hair, containing tetraoxyethylene lauryl ether and a cationic copolymer of vinylimidazolium methochloride and vinyl pyrrolidone.

Usually agents to set and care for hair consist of solutions of film-forming natural or synthetic polymers. Such natural polymers are shellac, alginates, gelatines, pectines, chitosan salts, and cellulose derivatives. Synthetic polymers that can be used are, for example, polyvinylpyrrolidone, polyvinyl acetate, polyacryl compounds such as acrylic acid or methacrylic acid polymers, basic polymers of esters of these two acids with aminoalcohols or the salts or quarternization products of these basic polymers, polyacrylnitrile, and copolymers of such compounds, for example, polyvinylpyrrolidone vinyl acetate or polyvinylpyrrolidone dimethylaminoethylmethacrylate.

In addition to the foregoing, agents used to care for hair and to strengthen a set in order to improve wet combability and the feel of the hair, particularly of damaged hair, frequently contain monomer quaternary ammonium compounds such as, for example, alkyltrimethylammonium chlorides, dialkylmethyl- ammonium chlorides, alkyldimethylbenzylammonium chlorides, and alkylpyridinium chlorides.

However, additives containing these kinds of quaternary ammonium compounds reduce the physiological compatibility of such preparations, in particular with regard to the eyes.

Our own DE-OS 34 01 037 describes a cosmetic agent for caring for and strengthening the hair comprising tetraoxyethylene laurylether and a quaternized copolymer of vinylpyrrolidone and dimethylaminoethylmethacrylate, in which an addition of such quarternary ammonium compounds is not required.

However, the hair-conditioning properties of these agents are not completely satisfactory, particularly in the case of damaged hair (see test example 1). Furthermore, because of the high price of the quaternized copolymers of vinylpyrrolidone and dimethylamino ethylmethylacrylate that are used, this agent is comparatively costly.

In contrast to this, it has now been found that a simultaneously outstanding conditioning and good strengthening of the hair can be achieved by the use of a synergistic combination of tetraoxyethylene lauryl ether and a cationic copolymer of vinylimidazolium methochloride and vinylpyrrolidone.

SUMMARY OF THE INVENTION

Accordingly, it is an object of the present invention to provide an agent for strengthening a hairdo and care of hair which is based on an aqueous, alcoholic or aqueous-alcoholic solution of a quaternized copolymer of vinylpyrrolidone and tetraoxyethylene lauryl ether and which is easier to use and results in more lusterous hair than agents of this type.

In keeping with these objects and with others which will become apparent hereinafter, the agent. contains: (a) 0.1 to 10.0 percent by weight of a cationic copolymer of vinylimidazolium methochloride and vinylpyrrolidone as quaternized copolymer of the vinylpyrrolidone and (b) 0.1 to 5.0 percent by weight tetraoxyethylene lauryl ether.

The commercially available products Luviquat FC 370 TM, Luviquat FC 550 TM, and Luviquat FC 905 TM produced by BASF AG, Ludwigshafen (Federal Republic of Germany) are especially suitable as the cationic copolymer of vinylimidazolium methochloride and vinylpyrrolidone. These copolymers (CTFA designation: polyquaternium-16) have the following formula (I):

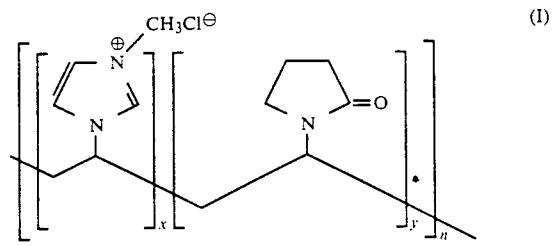

(I) wherein
$x = 0.30$ to $0.95$
$y = 0.05$ to $0.70$
$x + y = 1$, and where n = the number of repeating units and n is such that the mean molecular weight of the cationic copolymer of formula (I) is preferably between 40,000 g/mol and 1,000,000 g/mol.

Of the copolymers referred to, a copolymer of 95 mol-% vinylimidazolium methochloride and 5 mol-% vinylpyrrolidone (commercial designation Luviquat FC 905 TM, BASF) with a mean molecular weight of approximately 80,000, is particularly preferred. The tetraoxyethylene lauryl ether of formula (II)

$CH_3(CH_2)_{10}CH_2(OCH_2CH_2)_4OH$ (II) is a lauryl alcohol oxyethylated with 4 mol ethylene oxide.

The tetraoxyethylene lauryl ether is to be contained in the agent according to the present invention in a quantity of 0.1 to 5 percent by weight, preferably in a quantity of 0.5 to 2 percent by weight.

The content of the cationic copolymer of the component (a) amounts to 0.1 to 10 percent by weight, preferably 1 to 3.5 percent by weight.

The agent according to the present invention preferably has a pH between 2 and 11, and can be in the form of an aqueous, alcoholic or aqueous-alcoholic solution.

In this connection, the lower alcohols with 1 to 4 carbon atoms, such as ethanol and isopropanol, normally used in particular for cosmetic purposes, can be used. These alcohols can be contained in the agent according to the present invention in a quantity of 0 to 99.8 percent by weight.

Of course, the usual cosmetic hair additives, for example, perfume oils, vegetable extracts, bactericides or fungicides, anti-dandruff agents, solvents for perfume oils, natural or synthetic resins such as chitosan derivatives, polyvinylpyrrolidone and polyvinylpyrrolidonevinylacetate copolymers, can be contained in the agent according to the present invention, providing such additives appear useful and expedient. In addition, coloring agents for coloring the preparation, or dyes that act directly on the hair so as to simultaneously tone it can also be contained in the agent.

Of the latter dyes, which can be present either singly or in mixture, the following classes are mentioned: aromatic nitro dyes (for example, 1,4-diamino-2-nitro-benzene, picramic acid, 1-hydroxy-2-amino-4-nitro-benzene and 1,4-bis(2-hydroxyethyl)-amino-2-nitro-5-chlorobenzene), azo dyes (for example, C.I. 14 805 - acid brown 4), anthraquinone dyes (for example, C.I. 61 105 - disperse violet 4), and triphenylmethane dyes (for example, C.I. 42 535 - basic violet 1), said dyes of these classes having an acid, non-ionogenic or basic character depending on the type of their substituted groups. In the agent according to the present invention the overall concentration of these is usually approximately 0.01 to 2.0 percent by weight.

The agent according to the present invention can also be combined in a pressurized container, with a propellant added to it; in this case, the preparation is discharged as a foam, and can be easily and conveniently dispensed and spread on the hair by a valve that incorporates an applicator. Propellants that are suitable for this purpose are volatilized fluorochlorohydrocarbons, such as difluorodichloromethane or trichloromonofluoromethane, tetrafluorodichloroethane or lower alkanes, such a n-butane, i-butane, and propane, or dimethylether, or propellants that are gaseous at the pressures used here, such as $N_2$, $N_2O$, and $CO_2$, as well as mixtures of the above compounds. The propellants are best contained in these agents in an amount from approximately 2 to 10 percent by weight.

The agent according to the present invention is usually applied to the hair in a quantity from 5 to 20 grams, depending on the thickness of the hair, after it has been washed and dried with a towel. Next, the hair is combed, and either blown dry or first wound onto water-waving rollers and then dried.

The agent for setting and caring for the hair according to the present invention brings about a surprising and outstanding improvement of both the ease with which the hair can be combed when wet, and the lustre and feel of the hair when dry, whilst simultaneously improving its set. In particular, there is a marked improvement in the way in which a comb or brush moves through the wet hair after the agent according to the present invention has been applied to it, and this makes it much simpler to blow-dry the hair or wind it onto water-waving rollers. The advantages, described heretofore, of the combination of tetraoxyethylenelaurylether and a copolymer of vinylimidazolium methochloride and vinylpyrrolidoneaccording to the present invention, described above, are particularly plain when it is applied to severely damaged hair.

Because of its excellent effect in improving the combability, it has been possible to dispense with the use of quarternary ammonium compounds in the agent for setting and caring for the hair according to the present invention, providing one adds it to the agent in a low concentration (approximately up to 0.2 percent by weight) as a preservative in order to impart bactericidal and fungicidal properties to it.

A further advantage of the agent according to the present invention is its low price in comparison with agents known from the literature, for example DE-OS 34 01 037. Thus, the copolymer of vinylimidazolium methochloride and vinylpyrrolidone that is used as component (a) costs only one-third the price of the cationic copolymer that is used in DE-OS 34 01 037.

The outstanding improvement of the combability of wet hair and the improvement of lustre and feel which have been observed are surprising and can only be explained synergistically, since the tetraoxyethylene lauryl ether or the cationic copolymer of vinylimidazolium methochloride and vinylpyrrolidone in suitable solution applied alone to the hair (see test examples C and D) cause only a slight and unsatisfactory improvement of the criteria cited herein.

Furthermore, the following test examples E, F, G, and H have shown that fatty alcohol polyoxyethylene ethers other than tetraoxyethylene lauryl ether do not display the synergistic effect that is required for use in the agent according to the present invention.

The invention will now be described in more detail with reference to the accompanying non-limiting examples.

EXAMPLE 1

An agent in the form of an aqueous solution

| | |
|---|---|
| 1.2 g | tetraoxyethylene laurylether |
| 2.5 g | cationic copolymer of vinylimidazolium methochloride and vinylpyrrolidone in the proportion 95:5 |
| 96.3 g | water, completely desalinated |
| 100.0 g | |

EXAMPLE 2

An agent in the form of an aqueous-alcoholic solution

| | |
|---|---|
| 0.7 g | tetraoxyethylene laurylether |
| 2.0 g | cationic copolymer of vinylimidazolium methochloride and vinylpyrrolidone in the proportion 95:5 |
| 20.0 g | ethanol |
| 77.3 g | water, completely desalinated |
| 100.0 g | |

EXAMPLE 3

An agent packed under pressurized gas

| | |
|---|---|
| 1.5 g | tetraoxyethylene laurylether |
| 2.5 g | cationic copolymer of vinylimidazolium methochloride and vinylpyrrolidone in the proportion 95:5 |
| 10.0 g | isopropanol |
| 86.0 g | water, completely desalinated |
| 100.0 g | |

Charge: 96.0 g liquid of the above composition 4.0 g propane

EXAMPLE 4

An agent packed under pressurized gas

| | |
|---|---|
| 1.4 g | tetraoxyethylene laurylether |
| 2.0 g | cationic copolymer of vinylimidazolium methochloride and vinylpyrrolidone in the proportion 50:5 |
| 8.0 g | ethanol |
| 88.6 g | water, completely desalinated |
| 100.0 g | |

Charge: 96.0 g liquid of the above composition 2.0 g propane 1.6 g butane, 0.4 g dimethylether

EXAMPLE 5

An agent in the form of an aqueous-alcoholic solution

| | |
|---|---|
| 1.20 g | tetraoxyethylene laurylether |
| 2.50 g | cationic copolymer of vinylimidazolium methochloride and vinylpyrrolidone in the proportion 30:70 |
| 0.50 g | polyvinylpyrrolidone |
| 0.05 g | basic violet (C.I. No.42 535) |
| 5.00 g | ethanol |
| 90.75 g | water, completely desalinated |
| 100.0 g | |

All of the percentage figures quoted in the above application are percentages by weight.

TEST EXAMPLES

TEST EXAMPLE A

Once washed, the hair of 20 test subjects, which had been hand dried with a towel, was treated with an agent as described in Example 1.

Ten of the test subjects had normal hair. The remaining 10 subjects had hair that was damaged or severely damaged. In order to obtain clear results and eliminate the problem of hair quality that varied from subject to subject, that hair was parted at the centre and 2.4 to 6 g of the agent, depending on the thickness of the hair, was applied to one half of the hair, whereas the other half was left untreated. Next, each half of the hair was combed, wound onto waterwaving rollers, and dried.

Finally, the rollers were removed and the hair was styled. This meant that the effect of the preparation could be properly assessed by a group of expert hairdressers. An assessment was made according to a schedule of combined criteria for combability when wet, retention of set, curliness, lustre, feel, and the charge of static electricity in the hair.

Grading:
1 = very good, 2 = good, 3 = satisfactory, 4 = less than satisfactory

The results of the test for that half of the hair that was treated compared to the untreated half are set out in the following table 1.

TABLE 1

| | Grade 1 | Grade 2 | Grade 3 | Grade 4 |
|---|---|---|---|---|
| Number of Test subjects | 18 | 1 | 1 | 0 |

TEST EXAMPLE B

The hair of a further group of 18 test subjects was treated in the same manner as described in test example A, using an agent as described in example 3. Ten test subjects of the group had hair that varied from damaged to severely damaged. The remaining eight subjects had normal hair. The results of these tests are set out in the following table 2.

TABLE 2

| | Grade 1 | Grade 2 | Grade 3 | Grade 4 |
|---|---|---|---|---|
| Number of Test subjects | 16 | 2 | 0 | 0 |

TEST EXAMPLE C

In order to examine the synergistic effect, the hair of a further group of 14 test subjects was treated on half sides with a composition as described in example 1, as described in test example A, although in this instance the tetraoxyethylene laurylether was replaced by an equal quantity of water. The other half of the hair was left untreated. Five of the test subjects had normal hair, and nine of the subjects had damaged hair. The results obtained from this test are set out in the following table 3.

TABLE 3

| | Grade 1 | Grade 2 | Grade 3 | Grade 4 |
|---|---|---|---|---|
| Number of Test subjects | 0 | 2 | 7 | 5 |

TEST EXAMPLE D

In order to further test the synergistic effect, a fourth group of 13 test subjects, of which six had normal hair and seven had severely damaged hair, were treated on half sides of their hair with a composition as described in example 1, as set out in test example A, although in this instance the agent contained no cationic copolymer of vinylimidazoliummethochloride and vinylpyrrolidone. In the composition as in example 1, the cation active copolymer was replaced by the corresponding weight fraction of water. The second half of the hair was left untreated. The results of the test are set out in the following table 4.

TABLE 4

| | Grade 1 | Grade 2 | Grade 3 | Grade 4 |
|---|---|---|---|---|
| Number of Test subjects | 0 | 2 | 6 | 5 |

A comparison of tables 1 and 2, and of tables 3 and 4 shows clearly that the combination contained in the agent according to the present invention has a synergistic effect compared to the effect achieved by the individual components.

TEST EXAMPLE E

The hair of a group of 10 test subjects, which ranged from damaged to severely damaged, was treated as in test example A, on half of the head, with a preparation made up as in example 1, although in this instance the tetraoxyethylene laurylether had been replaced by an equal quantity of trioxyethylene stearylether. The other side of the head was left untreated. The results of the test are set out in the following table 5.

TABLE 5

| | Grade 1 | Grade 2 | Grade 3 | Grade 4 |
|---|---|---|---|---|
| Number of Test subjects | 0 | 2 | 5 | 3 |

TEST EXAMPLE F

The hair of a group of 10 test subjects, which varied from damaged to severely damaged, was treated on half the head as described in test example A, using a preparation made up as described in example 1, although the tetraoxyethylene laurylether had been replaced by an equal quantity of decaoxyethylene isostearylether. The other side of the hair was left untreated. The results obtained in this test are set out in the following table 6.

TABLE 6

|  | Grade 1 | Grade 2 | Grade 3 | Grade 4 |
|---|---|---|---|---|
| Number of Test subjects | 0 | 2 | 6 | 2 |

The above test examples E and F demonstrate that amongst the polyoxyethylene laurylethers, only tetraoxyethylene laurylether has a markedly synergistic effect.

TEST EXAMPLE G

A further group of test subjects with hair which ranged from damaged to severely damaged was treated as in test example A, on half of the head, with a preparation made up as in example 1, although in this instance the tetraoxyethylene laurylether had been replaced by an equal quantity of trioxyethylene laurylether. The other side of the head was left untreated. The results of the test are set out in the following table 7.

TABLE 7

|  | Grade 1 | Grade 2 | Grade 3 | Grade 4 |
|---|---|---|---|---|
| Number of Test subjects | 0 | 4 | 5 | 1 |

TEST EXAMPLE H

Another group of ten test subjects with hair which ranged from damaged to severely damaged was treated as in test example A, on half of the head, with a preparation made up as in example 1, although in this instance the tetraoxyethylene laurylether had been replaced by an equal quantity of pentaoxyethylene laurylether. The other side of the head was left untreated. The results of the test are set out in the following table 8.

TABLE 8

|  | Grade 1 | Grade 2 | Grade 3 | Grade 4 |
|---|---|---|---|---|
| Number of Test subjects | 0 | 5 | 5 | 0 |

The results of the above test examples E to H show that fatty alcohol polyoxyethylene ethers other than tetraoxyethylene laurylether are not suitable for use according to the present invention.

The surprising and excellent synergistic improvement of the hair-conditioning properties and the very good set imparted to the hairstyle, in particular in the case of severely damaged hair, is restricted, according to the test results described above, to the combination of tetraoxyethylene laurylether with a cationic copolymer of vinylimidazolium methochloride and vinylpyrrolidone, and cannot be achieved with other fatty alcohol polyoxyethylene ethers.

TEST EXAMPLE I

An agent as described in example 1 of the present invention (agent I) was compared with an agent as in example 1 of DE-OS 34 01 037 (agent II) in a half-head test.

To this end, the already washed hair of twelve test subjects, which had been towel dried, and which varied from moderately to severely damaged, was treated in a parallel comparison with agent I and agent II. In order to obtain clear results and eliminate the problem of hair quality that varied from subject to subject, that hair was parted at the centre and 2.4 to 6 g of the agent I, depending on the thickness of the hair, was applied to one half of the hair, whereas the other half was treated with an equal quantity of agent II. Next, each half of the hair was combed, wound onto water-waving rollers, and dried.

Finally, the rollers were removed and the hair was styled. The result of assessment by expert hairdressers are set out in the following table 9.

TABLE 9

|  | Agent I | Agent II |
|---|---|---|
| Ease with which comb and brush pass through wet hair | very good | satisfactory |
| Lustre and feel of dry hair | very good | satisfactory |
| Ease of styling and retention of style applied | good | good |

As the foregoing comparative test shows, the agent (I) according to the present invention is clearly superior to the agent (II), known from DE-OS 34 01 037, in regard to its properties that improve combability as well as lustre and feel of the hair treated therewith.

While the invention has been illustrated and described as embodied in an agent for strengthening of a hairdo and care of hair, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of the prior art, fairly constitute essential characteristics of the generic or specific aspects of this invention.

What is claimed as new and desired to be protected by Letters Patent is set forth in the appended claims.

We claim:

1. An aqueous, alcoholic or aqueous-alcoholic agent for strengthening a hairdo and for care of hair comprising:

(a) 0.1 to 10 percent by weight of a cationic copolymer of vinylpyrrolidone and vinylimidazolium methochloride having structural formula (I)

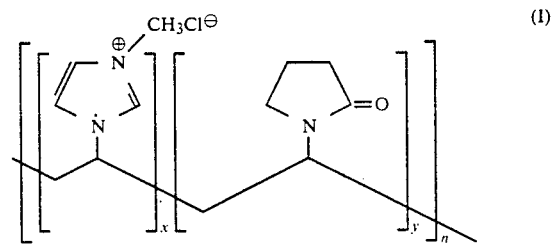

wherein $x = 0.30$ to $0.95$, $y = 0.05$ to $0.70$, and $x + y = 1$, and n being such that said cationic polymer has a molecular weight of from 40000 to 1000000 g/mol, and (b) 0.1 to 5 percent by weight tetraoxyethylene lauryl ether.

2. An agent according to claim 1, further comprising from 0 to 99.8% by weight of alcohol.

3. An agent according to claim 1, containing 1 to 3.5 percent by weight of said cationic copolymer of vinylimidazolium methochloride and vinylpyrrolidone.

4. An agent according to claim 1, containing 0.5 to 2.0 percent by weight of said tetraoxyethylene lauryl ether.

5. An agent according to claim 1, further comprising 0.01 to 2.0 percent by weight of a dye that acts directly on said hair to provide simultaneous toning of said hair.

6. An agent according to claim 5, wherein said dye is selected from the group consisting of aromatic nitro dyes, azo dyes, anthraquinone dyes and triphenylmethane dyes.

7. An agent according to claim 1, further comprising 2 to 10 percent by weight of a propellant.

8. An agent according to claim 7, wherein said propellant is selected from the group consisting of n-butane, i-butane, propane, difluorodichloromethane, trichloromonofluoromethane, tetrafluorodichloroethane, dimethyl ether, $N_2$, $N_2O$ and $CO_2$ and mixtures thereof.

9. An agent according to claim 1, further comprising from 0 to 96.3% by weight of water.

10. An agent according to claim 2, wherein said alcohol is a lower alcohol having from one to four carbon atoms.

11. An agent according to claim 1, further comprising a 3.8:1 to 18.2:1 mixture of water and alcohol.

* * * * *